United States Patent
Kressner et al.

[11] Patent Number: 6,021,538
[45] Date of Patent: Feb. 8, 2000

[54] BRUSH SECTION FOR AN ELECTRIC TOOTHBRUSH

[75] Inventors: Gerhard Kressner, Altenstadt; Georges Driesen, Weilrod, both of Germany

[73] Assignee: Braun Aktiengesellschaft, Frankfurt, Germany

[21] Appl. No.: 08/986,254

[22] Filed: Dec. 5, 1997

[30] Foreign Application Priority Data

Jun. 24, 1995 [DE] Germany ................. 195 23 016

[51] Int. Cl.⁷ ............... A61C 17/34; A46B 13/02
[52] U.S. Cl. ............... 15/28; 15/207.2; 15/DIG. 5
[58] Field of Search ............ 15/22.1, 28, 167.1, 15/207.2, DIG. 5, DIG. 6

[56] References Cited

U.S. PATENT DOCUMENTS

| 4,020,522 | 5/1977 | Behrend | 15/28 |
| 4,739,532 | 4/1988 | Behrend | 15/28 |
| 5,467,495 | 11/1995 | Boland et al. | 15/28 |
| 5,652,990 | 8/1997 | Driesen et al. | 15/28 |
| 5,732,433 | 3/1998 | Gocking et al. | 15/22.1 |

FOREIGN PATENT DOCUMENTS

| 2587183 | 3/1987 | France . |
| WO 91 07116 | 5/1991 | WIPO . |
| WO 94 21192 | 9/1994 | WIPO . |

*Primary Examiner*—Terrence R. Till
*Attorney, Agent, or Firm*—Fish & Richardson P.C.

[57] ABSTRACT

The invention is directed to a brush section (24) for an electric toothbrush (20) in which a handle section (22) is connectible with the brush section (24). A bristle carrier (44) of a circular disk shaped configuration is arranged at the end of the brush section (24) remote from the handle section (22) and has on its upper side bristle tufts (46, 60, 62, 72, 74) disposed on one central ring (54) and one outer ring (56). The bristle carrier (44) is mounted on the brush section (24) so as to be rotatable about an axis of rotation (50) in an alternating oscillating fashion from a central position (58). The axis of rotation (50) is aligned at approximately right angles to a longitudinal center line (52) of the brush section (24). In use of the electric toothbrush (20), an improved cleaning action is accomplished in that the outer ring (56) of the bristle carrier (44) is set with tufts (60, 62) of bristles of different lengths.

39 Claims, 5 Drawing Sheets

| | | | | |
|---|---|---|---|---|
| ○ | 52 ± 2 | 6 | 7.5 ± 0.1 | 1.50 |
| ⊜ | 52 ± 2 | 6 | 7.5 ± 0.1 | 1.50 |
| ⦀ | 52 ± 2 | 6 | 8.2 ± 0.1 | 1.50 |
| TUFT | BRISTLES PER TUFT | BRISTLE DIAMETER [mil] | BRISTLE LENGTH [mm] | BORE DIAMETER [mm] |

| | | | | |
|---|---|---|---|---|
| ● | 58 ± 2 | 5 | 7.5 ± 0.1 | 1.30 |
| ⊜ | 52 ± 2 | 6 | 7.5 ± 0.1 | 1.50 |
| ◉ | 52 ± 2 | 6 | 8.2 ± 0.1 | 1.50 |
| TUFT | BRISTLES PER TUFT | BRISTLE DIAMETER [mil] | BRISTLE LENGTH [mm] | BORE DIAMETER [mm] |

| TUFT | BRISTLES PER TUFT | BRISTLE DIAMETER [mil] | BRISTLE LENGTH [mm] | BORE DIAMETER [mm] |
|---|---|---|---|---|
| ◉ | 58 ± 2 | 5 | 7.5 ± 0.1 | 1.30 |
| ⊜ | 52 ± 2 | 6 | 7.5 ± 0.1 | 1.50 |
| ⦵ | 52 ± 2 | 6 | 8.2 ± 0.1 | 1.50 |

| | | | | |
|---|---|---|---|---|
| ● | 58 ± 2 | 5 | 7.0 ± 0.1 | 1.30 |
| ◉ | 52 ± 2 | 6 | 8.0 ± 0.1 | 1.50 |
| TUFT | BRISTLES PER TUFT | BRISTLE DIAMETER [mil] | BRISTLE LENGTH [mm] | BORE DIAMETER [mm] |

BRUSH SECTION FOR AN ELECTRIC TOOTHBRUSH

BACKGROUND OF THE INVENTION

This invention relates to a brush section for an electric toothbrush, with a handle section connectible with the brush section, a bristle carrier of an in particular circular disk shaped configuration which is arranged at the end of the brush section remote from the handle section and has on its upper side bristle tufts disposed at least on one central ring and one outer ring, said bristle carrier being mounted on the brush section so as to be rotatable about an axis of rotation, in particular in an alternating oscillating fashion from a central position, and said axis of rotation being aligned angularly, in particular at right angles to a longitudinal center line of the brush section.

A brush section of this type for an electric toothbrush is known from International Patent Application WO 91/07116. In this specification, the bristles of the tufts disposed on the outer ring and the central ring of the bristle carrier are all of approximately equal length. This enables a user to clean uniformly in particular the tooth surfaces.

In a brush section for an electric toothbrush as disclosed in International Patent Application WO 94/21192, the bristles of the tufts disposed on the bristle carrier differ in length. In particular it is proposed in this specification that tufts comprised of longer bristles be arranged on a diameter within an outer ring. These longer bristle tufts thus enable the user to accomplish a better dental cleaning operation in particular on the interproximal spaces.

SUMMARY OF THE INVENTION

On the basis of the foregoing, it is an object of the present invention to provide a brush section for an electric toothbrush which enables a still further improved cleaning of the teeth, in particular of the interproximal spaces.

This object is accomplished in a brush section of the type initially referred to in that the outer ring is set with tufts of bristles of different lengths.

When tests were conducted, this arrangement of the longer bristle tufts in the outer ring of the bristle carrier has proven to be particularly advantageous. With this arrangement, a particularly good interproximal cleaning operation can be accomplished. This is presumably so because during dental cleaning the shorter bristle tufts on the outer ring of the bristle carrier take support upon the tooth surface, thus enabling the longer bristle tufts on the outer ring to penetrate between the user's teeth completely. In this manner, the longer tufts on the outer ring produce a thorough cleaning action on the interproximal spaces, while at the same time the shorter bristle tufts on the outer ring clean the tooth surfaces uniformly.

In an advantageous further development of the present invention, fourteen bristle tufts are arranged on the outer ring, comprising a cluster of four adjacent short bristle tufts, a cluster of three adjacent long bristle tufts, a cluster of four adjacent short bristle tufts, and a cluster of three adjacent long bristle tufts. Each cluster of tufts thus fills a sector of the outer ring. In this manner, the long and the short bristle tufts are each disposed in diametrically opposed sectors of a circle. As a result, the long and the short bristle tufts are symmetrically disposed on the outer ring of the bristle carrier. This has proven to be a particularly advantageous arrangement for cleaning the interproximal spaces.

The reason for this is presumably that in dental cleaning the long bristle tufts provided in the two sectors are able to penetrate the interproximal spaces on either side of a neck for cleaning, while the shorter bristle tufts contribute to supporting the bristle carrier on the tooth surface and thus to the cleaning thereof.

In an advantageous aspect of the present invention, in the central position of the bristle carrier the sectors with the long bristle tufts are arranged along the longitudinal center line, and the sectors with the short bristle tufts are arranged transversely to the longitudinal center line. This has proven to be particularly advantageous for the manipulation of the electric toothbrush. When a user holds the electric toothbrush approximately parallel to his upper or lower jaw for cleaning his teeth, the long bristle tufts are able to penetrate and clean the interproximal spaces.

In an advantageous further development of the present invention, the bristle tufts or the clusters of bristle tufts of different length each differ in color. Because of the severer load placed upon them, it is particularly suitable to make provision for the long bristle tufts to be comprised of color indicator bristles, in particular of green or blue bristles. This makes it easy for the user to make a visual distinction between long and short bristle tufts. The advantage thereby achieved is that it is by reason of this visual impression alone that the user aligns the electric toothbrush properly, thereby enabling the described improved cleaning action to be accomplished by the tufts with the longer bristles without any further action being necessary.

In an advantageous further development of the present invention, the tufts on the central ring are comprised of bristles of a substantially uniform length corresponding approximately to the bristle length of the short bristle tufts on the outer ring. This has the advantage that it is not only the short bristle tufts on the outer ring that are used for bearing against the tooth surface as explained, but also the equally short bristle tufts on the central ring. Particularly suitably, the adjacent tufts on the central ring lying radially inwardly relative to the long bristle tufts on the outer ring are comprised of color indicator bristles, in particular of green or blue bristles. The colored tufts on the central ring and on the outer ring thereby form diametrically opposed wedges. This further enhances the described visual effect of an automatically correct alignment of the electric toothbrush by its user.

In an advantageous further development of the present invention, at least two short bristle tufts are provided in an inner zone of the bristle carrier, their arrangement being preferably at about right angles to the central position of the bristle carrier. These serve, as the short bristle tufts on the outer ring and the central ring, for further supporting the bristle carrier on the tooth surface.

Further features, advantages and application possibilities of the present invention will become apparent from the subsequent description of embodiments illustrated in more detail in the accompanying drawings. It will be understood that any single feature and any meaningful combination of single features described and/or represented by illustration form the subject matter of the present invention, irrespective of their summary in the claims and their back-reference.

BREIF DESCRIPTION OF THE DRAWINGS

DETAILED DESCRIPTION

Figure 1:
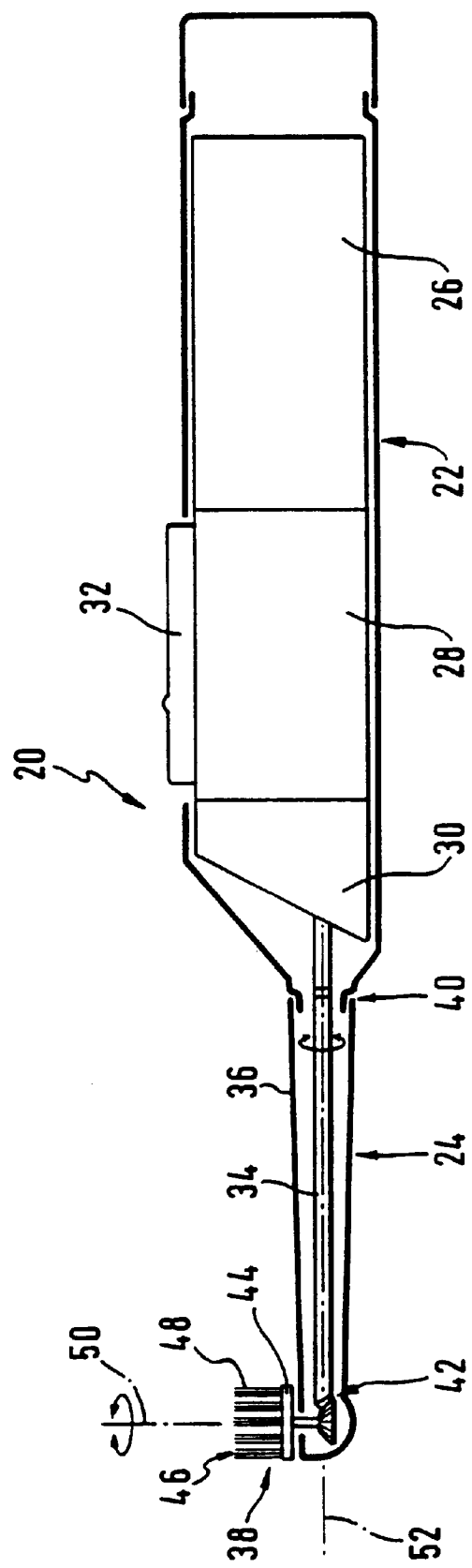
FIG. 1 is a schematic side view of an electric toothbrush.

Referring now to FIG. 1 of the drawings, reference numeral 20 designates an electric toothbrush. The toothbrush 20 comprises handle section 22 and a brush section 24 adapted to be coupled therewith. The handle section 22 accommodates a secondary battery 26 or, alternatively, a primary battery, an electric motor 28, and a motion converting mechanism 30 for converting the continuous rotary motion of the electric motor 28 into an oscillatory motion. Provided on the outside of the handle section 22 is a switch 32 for activating the toothbrush 20. The brush section 24 includes a hollow mounting tube 36 receiving a shaft 34. The mounting tube 36 and the shaft 34 are connectible with the handle section 22 by a coupling means 40. Arranged at the end of the brush section 24 remote from the handle section 22 is a brush 38 with a bristle carrier 44 for receiving the bristles 48 or bristle tufts 46. A bevel gear arrangement 42 at the end of the shaft 34 sets the brush 38 in an oscillatory motion. The range of the angle swept by the bristle carrier 44 during this motion is preferably of the order of about ±35 degrees±5 degrees, with values in the range from ±10 degrees to ±100 degrees being however also possible. The oscillation frequency may be between 10 Hz and 100 Hz, approximately, preferably at 40 Hz to 70 Hz, approximately. The axis of rotation 50 of the bristle carrier 44 forms with the axis of rotation 52 of the shaft 34 an angle of about 90 degrees. The toothbrush of FIG. 1 is described in detail in applicant's International Patent Application WO 91/07116 which is hereby incorporated by express reference in the disclosure content of the present application.

FIGS. 2 to 5 illustrate four embodiments of bristle carriers 44 differing from each other in respect of arrangement, configuration and selection of the individual tufts 46 or bristles 48. Schematically indicated in FIGS. 2 to 5 are the mounting tube 36 as well as the axis of rotation 52 of the shaft 34, which axis is approximately coincident with the longitudinal center line of the mounting tube 36 and thus of the brush section 24. The axis of rotation 50 of the bristle carrier 44 is illustrated in the center of FIGS. 2 to 5. The bristle carrier 44 is configured essentially as a circular plate with a diameter of between 11 mm and 15 mm, approximately, preferably 12 mm, approximately. The tufts 46 or bristles 48 are arranged on the upper side of the bristle carrier 44 on a central ring 54, an outer ring 56 and in an inner zone 84 or inner ring 88, which are all approximately concentric with the axis of rotation 50 of the bristle carrier 44. The representations of FIGS. 2 to 5 illustrate the bristle carrier 44 in a central position 58, that is, the position occupied by the bristle carrier 44 as it passes through 0 degrees in its oscillatory rotational motion of ±35 degrees.

Figure 2:
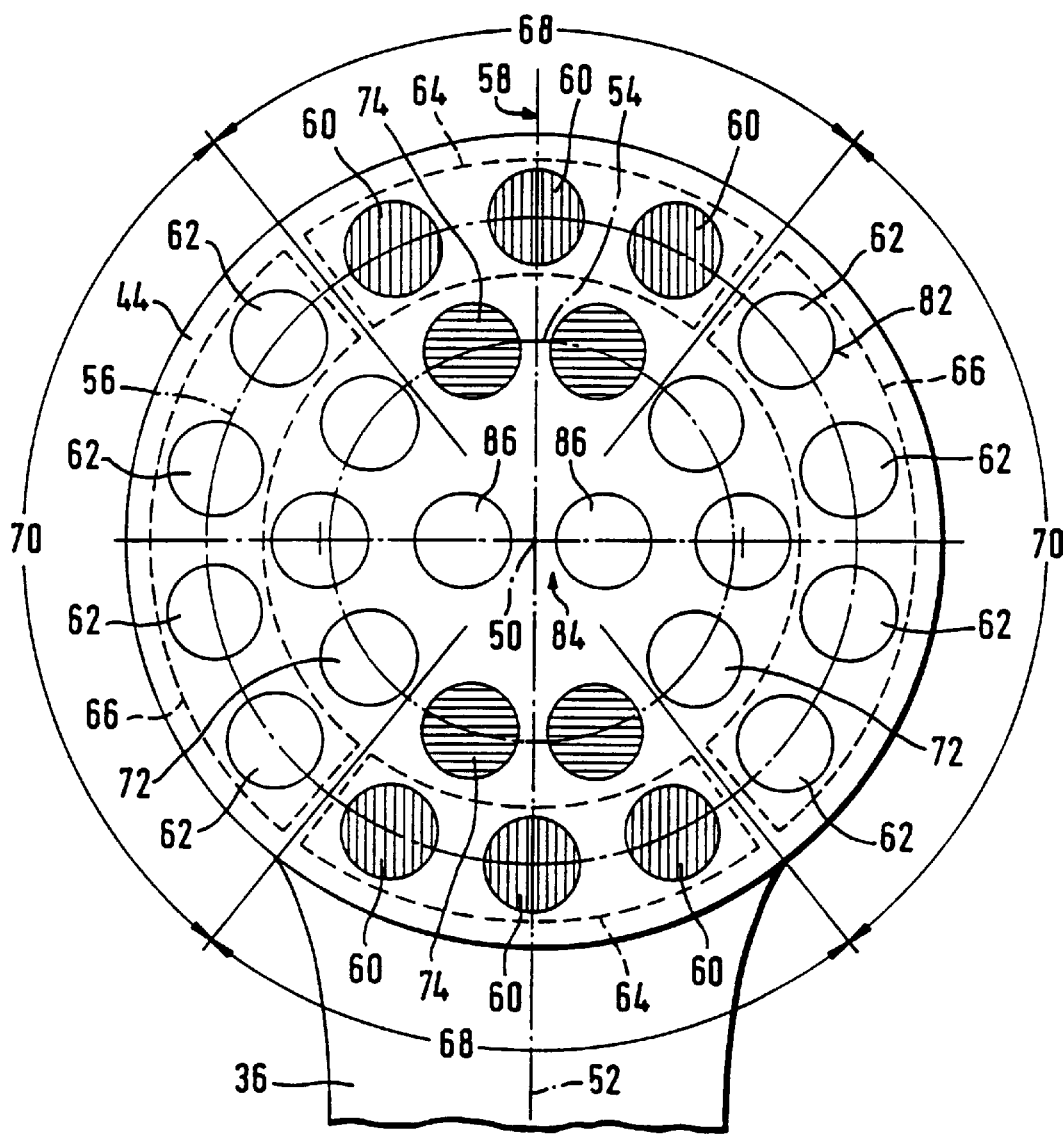
FIG. 2 is a schematic top plan view of the bristles illustrating a first embodiment of a bristle carrier for the electric toothbrush of FIG. 1.

In the first embodiment of the bristle carrier of FIG. 2, a total of fourteen tufts 60, 62 are disposed on the outer ring 56, the central ring 54 having a total of ten tufts 72, 74, and the inner zone 84 having two tufts 86.

Adjacent tufts 60, 62 on the outer ring 56 are combined or subdivided into four clusters 64, 66. Cluster 64 is comprised of three tufts 60 disposed symmetrically to the longitudinal center line 52 and extending over a sector 68 with a central angle of 80 degrees, approximately. Cluster 64 exists twice, being symmetrically disposed on either side of an imaginary transverse axis extending through the axis of rotation 50 at right angles to the longitudinal center line 52. The sectors 68 associated with the two clusters 64 thus extend approximately longitudinally to the longitudinal center line 52. Cluster 66 is comprised of four tufts 62 arranged symmetrically to said transverse axis and extending over a sector 70 with a central angle of 100 degrees, approximately. Cluster 66 exists twice, being symmetrically disposed on either side of the longitudinal center line 52. The sectors 70 associated with the two clusters 66 thus extend approximately transversely to the longitudinal center line 52.

The tufts 60 of the clusters 64 on the outer ring 56 are provided with long bristles of a length of about 8.2 mm±about 0.2 mm to 0.5 mm. The tufts 62 of the clusters 66 on the outer ring 56 are provided with short bristles of a length of about 7.5 mm±about 0.1 to 0.5 mm. The long and the short bristles of the tufts 60, 62 of both clusters 64, 66 have a diameter of 6 mils, approximately. The tufts 60, 62 of both clusters 64, 66 are comprised of about 54±4 such bristles. The bore diameter of the mounting bores 82 for the tufts 60, 62 in the bristle carrier 44 is 1.5 mm, approximately.

The long bristles of the tufts 60 and the short bristles of the tufts 62 differ in color. This can be accomplished in particular by color indicator bristles, for example, by green or blue bristles of this type which are used as long bristles of the tufts 60.

The ten tufts 72, 74 on the central ring 54 are arranged such that each two tufts 74 are associated with the area of the two sectors 68, and each three tufts 72 are associated with the area of the two sectors 70. In this arrangement, the two tufts 74 on the central ring 54 lie radially inwardly relative to the adjacent long bristle tufts 60 on the outer ring 56.

The bristles of the tufts 72, 74 on the central ring 54 are all of a uniform length amounting approximately to the length of the short bristles of the tufts 62 on the outer ring 56, that is, about 7.5 mm±about 0.1 to 0.5 mm. The diameter of their bristles is 6 mils, approximately (1 mil=0.0254 mm). About 54÷4 such bristles combine to form one of the tufts 72, 74. The bore diameter of the mounting bores 82 for the tufts 72, 74 in the bristle carrier 44 is 1.5 mm, approximately.

The two tufts 74 arranged in the respective area of the two sectors 68 differ in color from the other tufts 62, 72. This can be accomplished by configuring the bristles of the tufts 74 in particular as color indicator bristles of a blue or green color, for example.

Of the two tufts 86 in the inner zone 84, one each is arranged in the area of the two sectors 70. The two tufts 86 are thus disposed at approximately right angles to the longitudinal center line 52 and thus approximately transversely to the central position 58. The bristles of the tufts 86 have a length of about 7.5 mm±0.1 to 0.5 mm, the bristle diameter is 6 mils, approximately. Each of the two tufts 86 is comprised of about 54±4 bristles. The bore diameter of the mounting bores 82 for the tufts 86 is 1.5 mm, approximately. The area of the two sectors 68 in the inner zone 84 is devoid of tufts.

Accordingly, in the first embodiment of FIG. 2 all tufts 62, 72, 86 in the area of the two sectors 70 comprise bristles of approximately like length and approximately like diameter. By contrast, in the area of the two sectors 68, the tufts 60 in the outer ring 56 have longer bristles than the tufts 74 in the central ring 54. Further, the tufts 60, 74 in the two sectors 68 differ in color from the tufts 62, 72, 86 in the two sectors 70.

Figure 3:
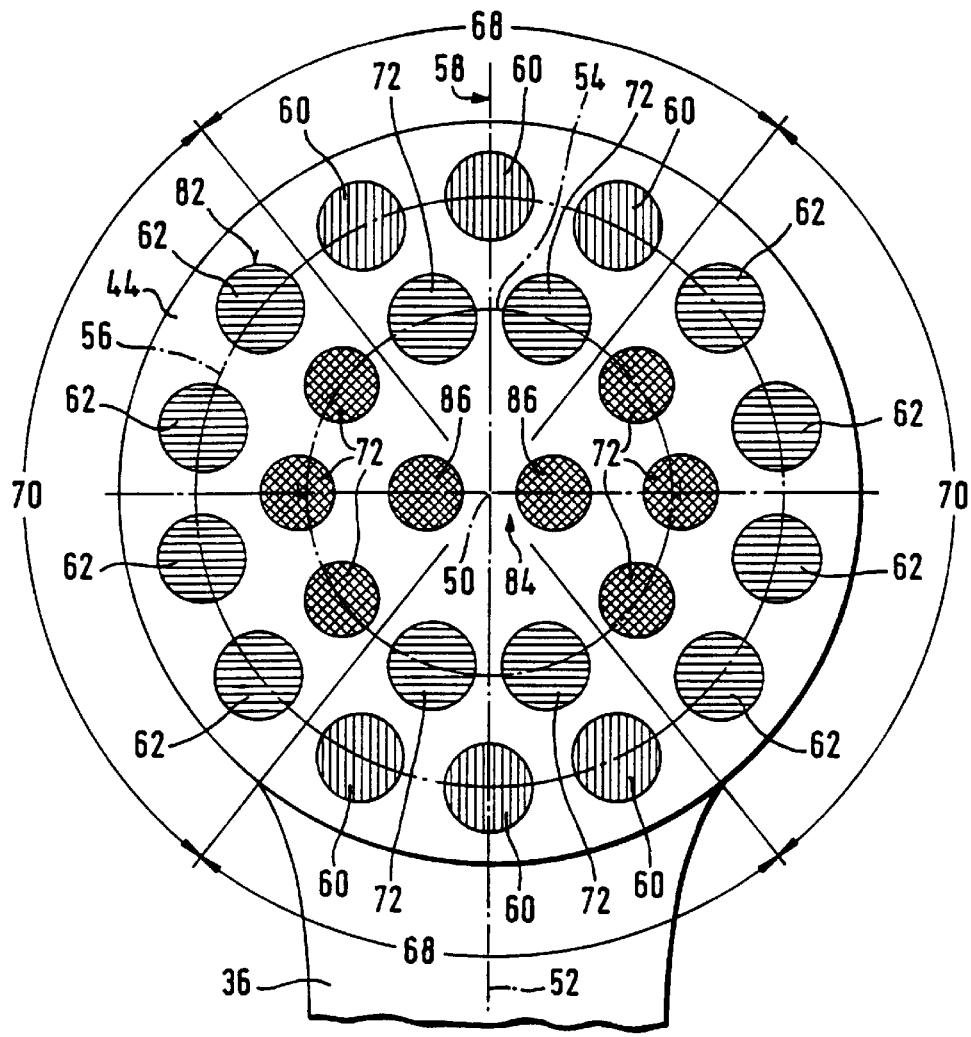
FIG. 3 is a schematic top plan view of the bristles illustrating a second embodiment of a bristle carrier for the electric toothbrush of FIG. 1.

In the second embodiment of FIG. 3, the sole difference to the first embodiment of FIG. 2 resides in that in the area of the two sectors 70 the tufts 62 on the outer ring 56 have bristles with a diameter greater than the bristles of the tufts 72, 86 on the central ring 54 and in the inner zone 84. As before, the bristles of the tufts 62 have a diameter of 6 mils, approximately, whereas the bristles of the tufts 72, 86 have a diameter of 5 mils, approximately. Thus, the bore diameter of the mounting bores 82 for the tufts 72, 86 is only 1.3 mm, approximately, and the bristles per tuft 72, 86 are in amount about 60±4. The length of the bristles of the tufts 62, 72, 86 remains unchanged at about 7.5 mm±0.1 mm to 0.5 mm.

Figure 4:
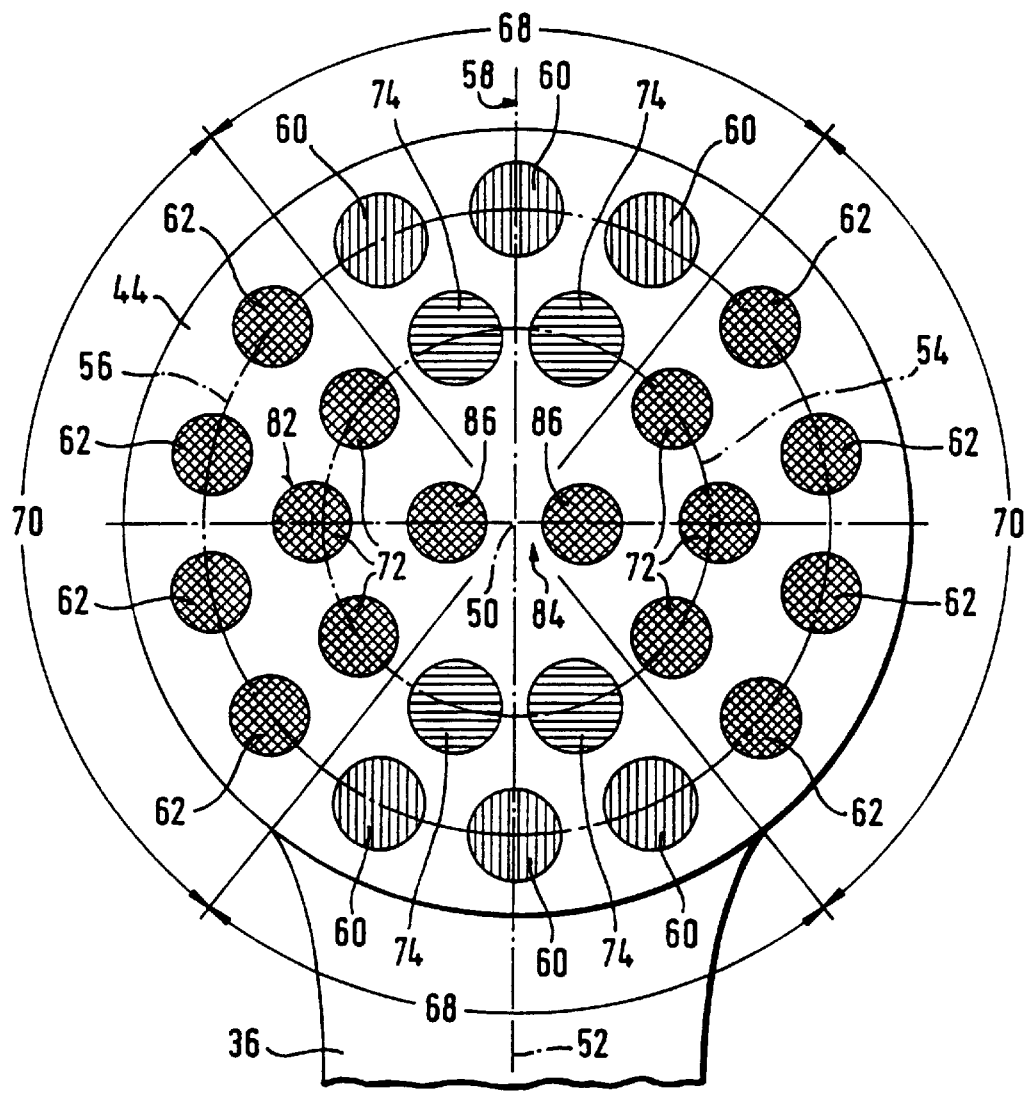
FIG. 4 is a schematic top plan view of the bristles illustrating a third embodiment of a bristle carrier for the electric toothbrush of FIG. 1.

In the third embodiment of FIG. 4, the sole difference to the first embodiment of FIG. 2 resides in that in the area of the two sectors 70 all of the tufts 62, 72, 86 on the outer ring 56, the central ring 54 and in the inner zone 84 have bristles of a diameter smaller than the bristles of the tufts 60 in the sectors 68. The bristles of the tufts 62, 72, 86 have a diameter of 5 mils, approximately. The bore diameter of the mounting bores 82 for the tufts 62, 72, 86 is 1.3 mm, approximately, and the bristles per tuft 62, 72, 86 are in amount about 60±4. The length of the bristles of the tufts 62, 72, 86 remains unchanged at about 7.5 mm±0.1 mm to 0.5 mm.

Figure 5:
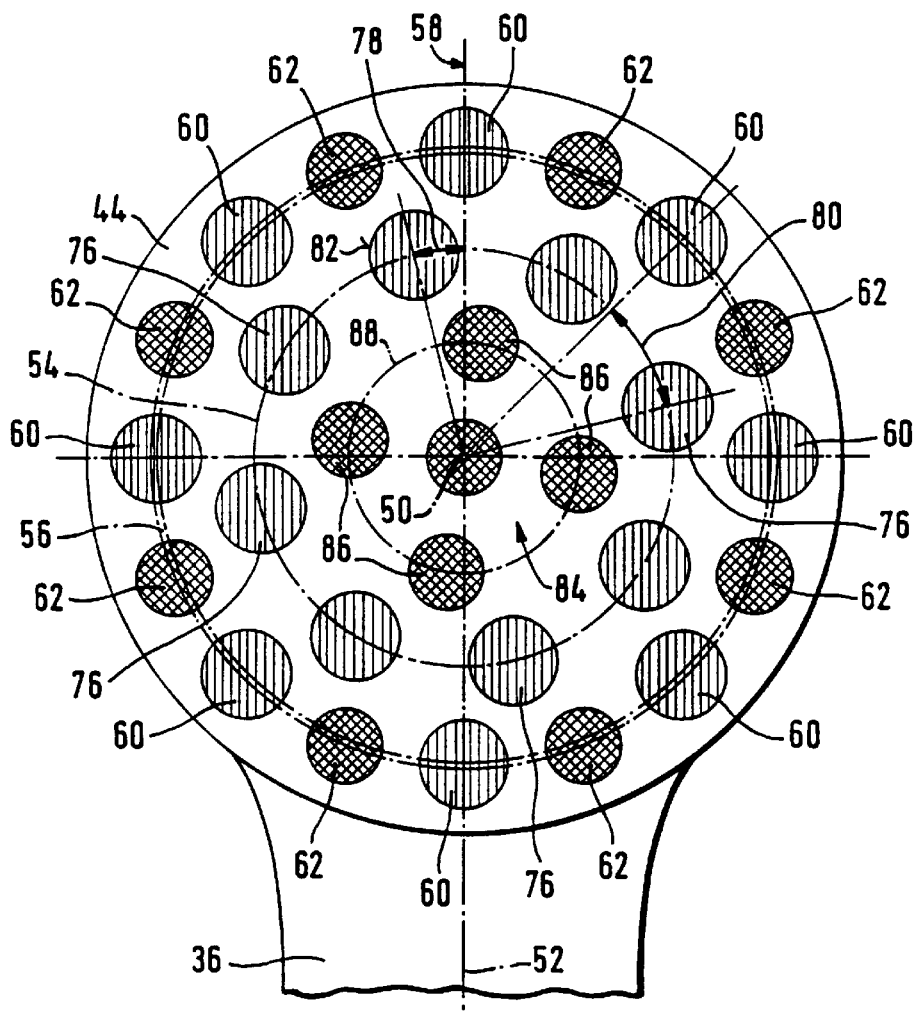
FIG. 5 is a schematic top plan view of the bristles illustrating a fourth embodiment of a bristle carrier for the electric toothbrush of FIG. 1.

In the fourth embodiment of the bristle carrier 44 of FIG. 5, a total of sixteen tufts 60, 62 are arranged on the outer ring 56, a total of eight tufts 76 are on the central ring 54, and four or five tufts 86 are arranged in the inner zone 84.

The tufts 60, 62 on the outer ring 56 are alternating long and short bristle tufts. The long bristles of the tufts 60 have a length of about 8.0 mm±0.1 mm to 0.5 mm, while the short bristles of the tuft's 62 are about 7.0 mm±0.1 mm to 0.5 mm long. The bristle diameter of the long bristle tufts 60 is 6 mils, approximately, and of the short bristle tufts 5 mils, approximately. The long bristle tufts 60 are comprised of about 54±4 bristles each, and the short bristle tufts 62 have about 60±4 bristles per tuft 62. The bore diameter of the mounting bores 82 for the long bristle tufts 60 in the bristle carrier 44 is about 1.5 mm, and for the short bristle tufts 62 about 1.3 mm.

The tufts 76 on the central ring 54 have bristles of a uniform length corresponding to the length of the long bristle tufts 60 on the outer ring 56. Accordingly, the tufts 76 have bristles of a length of about 8.0 mm±0.1 mm with a bristle diameter of 6 mils, approximately, comprising about 54±4 bristles per tuft 76 and with a diameter of the mounting bores 82 for the tufts 76 in the bristle carrier 44 of about 1.5 mm.

The tufts 76 on the central ring 54 are laterally offset in a radial direction relative to the adjacent long bristle tufts 60 on the outer ring 56. The amount of offset 78, 80 is about 0.5 to 1.5 times the diameter of the mounting bores 82 for the tufts 76.

In the inner zone 84 is an inner ring 88 on which the four tufts 86 are circumferentially spaced apart by about 90 degrees. In addition, the four tufts 86 on the inner ring 88 are interplaced between the eight tufts 76 on the central ring 54.

A further possibility is to arrange a fifth tuft 86 in the center of the bristle carrier 44.

The tufts 86 have bristles of a uniform length corresponding approximately to the length of the short bristle tufts 62 on the outer ring 56. The length of the tufts 86 is thus about 7.0 mm±0.1 mm to 0.5 mm with a bristle- diameter of 5 mils, approximately. The number of bristles per tuft 86 is about 60±4 with a bore diameter of about 1.3 mm for the mounting bores 82 for the tufts 86.

The long bristle tufts 60 on the outer ring 56 and the long bristle tufts 76 on the central ring 54 differ in color from the remaining tufts 62 on the outer ring 56 and the tufts 86 in the inner zone 84. This can be accomplished by using in particular color indicator bristles, for example, blue or green bristles for the tufts 60, 76.

The embodiments of bristle carriers 44 described may be operated in a variety of ways in combination with the electric toothbrush 20 equally described. Thus it is possible for the bristle carrier 44 to be set in an alternating oscillatory motion about the axis of rotation 50 at a frequency of about 62 Hz±5 Hz. The angle of oscillation is about ±30 degrees±5 to 10 degrees, relative to the central position 58, the amplitude of the bristle deflection is about ±3 to 4 mm, and the bristle speed is approximately between 0.5 m/s and 2 m/s, preferably in the range from 0.9 m/s to 1.7 m/s, in particular at about 1.3 m/s. This possibility may be varied, for example, by operating the bristle carrier 44 at a frequency of about 47 Hz±5 Hz, resulting in a bristle speed of about 0.9 m/s, with the other values remaining unchanged. Another possibility involves setting the bristle carrier 44 in an alternating oscillatory motion about the axis of rotation 50 at a frequency of about 115 Hz±20 Hz. In this case, the oscillation angle is about ±11 degrees±3 degrees relative to the central position 58, the amplitude of the bristle deflection is about 0.5 mm to 2.5 mm, preferably about 1 mm to 1.2 mm, and the bristle speed is approximately in the range from 0.6 m/s to 1.2 m/s, preferably at about 0.9 m/s. Further possibilities of driving the bristle carrier 44 comprise any combination of the above values, and it will be understood that the above combinations of values are not intended to limit the wide variety of these combinations.

We claim:

1. A brush section for an electric toothbrush having a handle section, the brush section comprising:
    a first end adapted to be connected to the handle section;
    a second end remote from the first end, the second end including a disk-shaped bristle carrier, the bristle carrier having an end surface which includes bristles arranged in the form of tufts, the tufts being disposed at least on one central ring and on one outer ring, the bristle carrier being mounted on the second end of the brush section so as to be rotatable about an axis of rotation in an alternating oscillating fashion from a central position, the axis of rotation being aligned at an angle to a longitudinal center line of the brush section, wherein the outer ring includes tufts having bristles of different lengths, and adjacent tufts on the outer ring form clusters of tufts, wherein each cluster of tufts has bristles of a length different from bristles of tufts of at least one other cluster.

2. The brush section as claimed in claim 1, wherein the outer ring is divided into sectors, each sector of the outer ring comprising clusters of tufts of different bristle length.

3. The brush section as claimed in claim 2, wherein the outer ring comprises four sectors, each sector defined by a central angle in the range from about 60 degrees to about 120 degrees.

4. The brush section as claimed in claim 2, further comprising tufts having longer bristles and tufts having shorter bristles, wherein the longer bristle tufts and the shorter bristle tufts are each disposed in diametrically opposed sectors of the outer ring.

5. The brush section as claimed in claim 4, wherein a longitudinal center line passes through the sectors having the longer bristle tufts, and the sectors having the shorter bristle tufts are arranged transversely to the longitudinal center line.

6. The brush section as claimed in claim 5, wherein the shorter bristle tufts have bristles of a length between about 7.0 mm and 8.0 mm, and the longer bristle tufts have bristles of a length between about 7.7 mm and 8.7 mm.

7. The brush section as claimed in claim 4, wherein the bristles have diameters of between about 5 and 6 mils (1 mil=0.0254 mm) with the longer bristle tufts comprising bristles of a thickness greater than a thickness of the bristles of the shorter bristle tufts.

8. The brush section as claimed in claim 1, wherein fourteen bristle tufts are arranged on the outer ring, comprising a cluster of four adjacent shorter bristle tufts, a cluster of three adjacent longer bristle tufts, a cluster of four adjacent shorter bristle tufts, and a cluster of three adjacent longer bristle tufts.

9. The brush section as claimed in claim 1, wherein the tufts of having bristles of different length differ in color.

10. The brush section as claimed in claim 9, wherein the longer bristle tufts comprise color indicator bristles.

11. The brush section as claimed in claim 1, wherein the tufts on the outer ring comprise bristles having a diameter of about 6 mils and comprise between about 50 and 58 bristles per tuft.

12. The brush section as claimed in claim 1, wherein the axis of rotation is aligned at approximately a right angle to a longitudinal center line of the brush section.

13. A brush section for an electric toothbrush having a handle section, the brush section comprising:
   a first end adapted to be connected to the handle section;
   a second end remote from the first end, the second end including a disk-shaped bristle carrier, the bristle carrier having an end surface which includes bristles arranged in the form of tufts, the tufts being disposed at least on one central ring and on one outer ring, the bristle carrier being mounted on the second end of the brush section so as to be rotatable about an axis of rotation in an alternating oscillating fashion from a central position, the axis of rotation being aligned at an approximately right angle to a longitudinal center line of the brush section, wherein the outer ring includes tufts having bristles of different lengths and wherein the tufts of different bristle length are arranged on the outer ring in an alternating fashion throughout the outer ring.

14. The brush section as claimed in claim 13, further comprising tufts having longer bristles and tufts having shorter bristles, wherein the longer bristle tufts have bristles of a length between about 7.5 mm and 8.5 mm, and the shorter bristle tufts have bristles of a length between about 6.5 mm and 7.5 mm.

15. The brush section as claimed in claim 14, further comprising tufts on the central ring which include bristles of a substantially uniform length.

16. The brush section as claimed in claim 15, wherein the tufts on the central ring have bristles of a length corresponding substantially to the length of the shorter bristles of the tufts on the outer ring.

17. The brush section as claimed in claim 16, wherein the tufts on the central ring have bristles of a length between about 7.0 mm and 8.0 mm, and a diameter of between about 5 and 6 mils and comprise between about 46 and 68 bristles per tuft.

18. The brush section as claimed in claim 15, wherein adjacent tufts on the central ring lying radially inwardly relative to the longer bristle tufts on the outer ring comprise color indicator bristles.

19. The brush section as claimed in claim 15, wherein the tufts on the central ring have bristles of a length corresponding substantially to the length of the longer bristles of the tufts on the outer ring.

20. The brush section as claimed in claim 19, wherein the tufts on the central ring are laterally offset in a radial direction relative to adjacent longer bristle tufts on the outer ring.

21. The brush section as claimed in claim 20, further comprising mounting bores for the tufts, wherein an amount of lateral offset of the tufts on the central ring relative to adjacent longer bristle tufts on the outer ring is between about 0.5 and 1.5 times a diameter of the mounting bores.

22. The brush section as claimed in claim 19, wherein the tufts on the central ring have bristles of a length of between about 7.9 mm and 8.1 mm and a diameter of 6 mils, approximately.

23. The brush section as claimed in claim 19, wherein the tufts on the central ring comprise color indicator bristles.

24. The brush section as claimed in claim 14, wherein the longer bristle tufts have bristles of a diameter of 6 mils, approximately, and the shorter bristle tufts have bristles of a diameter of 5 mils, approximately.

25. The brush section as claimed in claim 14, wherein the longer bristle tufts comprise color indicator bristles.

26. The brush section as claimed in claim 13, wherein sixteen bristle tufts are arranged on the outer ring.

27. The brush section as claimed in claim 13, further comprising at least two tufts in an inner zone of the bristle carrier.

28. The brush section of claim 27, wherein the two tufts provided in the inner zone are arranged approximately transversely to a central position of the bristle carrier.

29. The brush section as claimed in claim 27, wherein the tufts provided in the inner zone of the bristle carrier are arranged on an inner ring.

30. The brush section as claimed in claim 27, wherein the tufts in the inner zone have bristles of a length of between about 6.0 mm and 7.5 mm and a diameter of about 5 mils and comprise between about 56 and 64 bristles per tuft.

31. The brush section as claimed in claim 13, wherein the bristle carrier is adapted to be set in an alternating oscillatory motion about the axis of rotation at a frequency of between about 40 Hz and 75 Hz with an angle of oscillation of between about ±20 degrees and ±40 degrees, relative to a central position, an amplitude of bristle deflection of about ±3.3 mm, and a bristle speed of between about 0.9 m/s and 1.7 m/s.

32. The brush section of claim 31, wherein the bristle carrier oscillates at a frequency of between about 45 Hz and 62 Hz, the angle of oscillation is between about ±25 degrees and ±35 degrees, and the bristle speed is about 1.3 m/s.

33. The brush section as claimed in claim 13, wherein the bristle carrier is adapted to be set in an alternating oscillatory motion about the axis of rotation at a frequency of between about 95 Hz and 135 Hz, with an oscillation angle of between about 8 degrees and 14 degrees relative to a central position, an amplitude of bristle deflection of between about 0.5 mm and 2.5 mm and the bristle speed being between about 0.6 m/s and 1.2 m/s.

34. The brush section as claimed in claim 13, wherein the bristle carrier has a diameter of between 11 mm and 15 mm, approximately.

35. The brush section as claimed in claim 13, wherein the bristles of the tufts on the outer ring have a diameter of about 6 mils.

36. The brush section as claimed in claim 35, wherein the tufts comprise between about 50 and 58 bristles per tuft.

37. The brush section as claimed in claim 13, wherein the difference in length between the bristles of the tufts having bristles of different length is between about 0.5 mm and 1 mm.

38. The brush section of claim 37, wherein the difference in length between the bristles of the tufts having bristles of different length is about 0.7 mm.

39. A brush section for an electric toothbrush having a handle section, the brush section comprising:

a first end adapted to be connected to the handle section;

a second end remote from the first end, the second end including a disk-shaped bristle carrier, the bristle carrier having an end surface which includes bristles arranged in the form of tufts, the tufts being disposed at least on one central ring and on one outer ring, the bristle carrier being mounted on the second end of the brush section so as to be rotatable about an axis of rotation in an alternating oscillating fashion from a central position, the axis of rotation being aligned at an approximately right angle to a longitudinal center line of the brush section, wherein the tufts on the outer ring include two diametrically arranged clusters of tufts having longer bristles, the two diametrically arranged clusters being positioned substantially along the longitudinal center line of the brush section, and the other bristle tufts on the outer ring and on the central ring have bristles shorter than the longer bristles of the bristle tufts of the diametrically arranged clusters.

* * * * *